United States Patent
Kovarik (10) Patent No.: US 10,245,288 B2
(45) Date of Patent: Apr. 2, 2019

(54) METHOD AND SYSTEM FOR REDUCING THE LIKELIHOOD OF DEVELOPING NASH IN AN INDIVIDUAL DIAGNOSED WITH NON-ALCOHOLIC FATTY LIVER DISEASE

(71) Applicant: Joseph E. Kovarik, Englewood, CO (US)

(72) Inventor: Joseph E. Kovarik, Englewood, CO (US)

( * ) Notice: Subject to any disclaimer, the term of this patent is extended or adjusted under 35 U.S.C. 154(b) by 0 days.

(21) Appl. No.: 15/392,173

(22) Filed: Dec. 28, 2016

(65) Prior Publication Data

US 2017/0106026 A1 Apr. 20, 2017

Related U.S. Application Data

(63) Continuation-in-part of application No. 14/752,192, filed on Jun. 26, 2015, now Pat. No. 9,549,842, which is a continuation-in-part of application No. 14/225,503, filed on Mar. 26, 2014, now Pat. No. 9,445,936, which is a continuation of application No. 13/367,052, filed on Feb. 6, 2012, now Pat. No. 8,701,671, application No. 15/392,172, which is a continuation-in-part of application No. 15/270,034, filed on Sep. 20, 2016, now Pat. No. 9,750,802, which is a continuation-in-part of application No. 14/954,074, filed on Nov. 30, 2015, now Pat. No. 9,457,077, which is a continuation-in-part of application No. 14/574,517, filed on Dec. 18, 2014, now Pat. No. 9,408,880, application No. 15/392,173, which is a continuation-in-part of application No. 15/228,454, filed on Aug. 4, 2016, now Pat. No. 9,585,920, and a continuation-in-part of application No. 14/611,458, filed on Feb. 2, 2015, which is a continuation-in-part of application No. 14/502,097, filed on Sep. 30, 2014, now Pat. No. 9,010,340, which is a continuation of application No. 14/307,651, filed on Jun. 18, 2014, now Pat. No. 8,936,030, which is a continuation-in-part of application No. 14/079,054, filed on Nov. 13, 2013, now Pat. No. 8,757,173, which is a continuation of application No. 13/425,913, filed on Mar. 21, 2012, now Pat. No. 8,584,685.

(60) Provisional application No. 62/275,341, filed on Jan. 6, 2016, provisional application No. 61/556,023, filed on Nov. 4, 2011, provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013, provisional application No. 62/274,550, filed on Jan. 4, 2016, provisional application No. 61/467,767, filed on Mar. 25, 2011.

(51) Int. Cl.
| | | |
|---|---|---|
| A61F 5/00 | (2006.01) | |
| A61K 35/741 | (2015.01) | |
| A61K 35/745 | (2015.01) | |
| A61K 35/747 | (2015.01) | |

(52) U.S. Cl.
CPC .......... *A61K 35/741* (2013.01); *A61F 5/0003* (2013.01); *A61K 35/745* (2013.01); *A61K 35/747* (2013.01)

(58) Field of Classification Search
None
See application file for complete search history.

(56) References Cited

U.S. PATENT DOCUMENTS

| | | |
|---|---|---|
| 3,178,341 A | 4/1965 | Hamill et al. |
| 3,832,460 A | 8/1974 | Kosti |
| 4,136,162 A | 1/1979 | Fuchs et al. |
| 4,568,639 A | 2/1986 | Lew |
| 4,687,841 A | 8/1987 | Spilburg et al. |
| 4,720,486 A | 1/1988 | Spilburg et al. |
| 4,995,555 A | 2/1991 | Woodruff |
| 5,002,970 A | 3/1991 | Eby, III |
| 5,277,877 A | 1/1994 | Jeffrey et al. |
| 5,614,501 A | 3/1997 | Richards |
| 5,719,196 A | 2/1998 | Uhari |

(Continued)

FOREIGN PATENT DOCUMENTS

| | | |
|---|---|---|
| WO | PCT/US2008/080362 | 4/2009 |
| WO | WO 2011/020780 | 2/2011 |

(Continued)

OTHER PUBLICATIONS

Malaguarnera et al (Dig Dis Sci, 57:545-553, 2012).*

*Primary Examiner* — Brian Gangle
(74) *Attorney, Agent, or Firm* — Sheridan Ross P.C.

(57) ABSTRACT

A method for reducing the likelihood of developing liver cancer in an individual diagnosed with non-alcoholic fatty liver disease that involves providing an individual with an effective amount of a composition of bacteria modified using a Clustered Regularly Interspaced Short Palindromic Repeats-CRISPR-associated system (CRISPR-Cas) or Clustered Regularly Interspaced Short Palindromic Repeats from *Prevotella* and *Francisella* 1 (CRISPR/Cpf1) system so that the bacteria is able to produce a therapeutically effective amount of anti-bodies to oxidized low density lipoprotein, with the modified bacteria preferably being from the *Lactobacillus*, *Bifidobacterium*, and *Streptococcus* species; and most preferably including *L. reuteri* bacteria modified using CRISPR-Cas and/or Cpf1 systems so that it is able to survive the conditions in the duodenum and jejunum of the small intestine of a human.

13 Claims, 1 Drawing Sheet

(56) References Cited

U.S. PATENT DOCUMENTS

| | | |
|---|---|---|
| 6,054,143 A | 4/2000 | Jones |
| 6,139,861 A | 10/2000 | Friedman |
| 6,210,699 B1 | 4/2001 | Acharya |
| 6,287,610 B1 | 9/2001 | Bowling et al. |
| 6,569,474 B2 | 5/2003 | Clayton et al. |
| 6,599,883 B1 | 7/2003 | Romeo |
| 6,722,577 B2 | 4/2004 | Dobyns, III |
| 6,919,373 B1 | 7/2005 | Lam et al. |
| 7,087,249 B2 | 8/2006 | Burrell |
| 7,267,975 B2 | 9/2007 | Strobel et al. |
| 7,353,194 B1 | 4/2008 | Kerker et al. |
| 7,540,432 B2 | 6/2009 | Majerowski et al. |
| 7,820,420 B2 | 10/2010 | Whitlock |
| 7,862,808 B2 | 1/2011 | Isolauri et al. |
| 7,901,925 B2 | 3/2011 | Bojrab |
| 8,034,606 B2 | 10/2011 | Park et al. |
| 8,197,872 B2 | 6/2012 | Mills et al. |
| 8,349,313 B2 | 1/2013 | Smith et al. |
| 8,420,074 B2 | 4/2013 | Rehberger et al. |
| 8,454,729 B2 | 6/2013 | Mittelmark et al. |
| 8,481,299 B2 | 7/2013 | Gueniche |
| 8,496,914 B2 | 7/2013 | Bonfiglio |
| 8,585,588 B2 | 11/2013 | Kovarik et al. |
| 8,685,389 B2 | 4/2014 | Baur |
| 8,701,671 B2 | 4/2014 | Kovarik |
| 8,716,327 B2 | 5/2014 | Zhao |
| 8,758,764 B2 | 6/2014 | Masignani et al. |
| 8,815,538 B2 | 8/2014 | Lanzalaco et al. |
| 8,865,211 B2 | 10/2014 | Tzannis |
| 8,951,775 B2 | 2/2015 | Castiel |
| 8,999,372 B2 | 4/2015 | Davidson |
| 9,011,834 B1 | 4/2015 | McKenzie et al. |
| 9,017,718 B2 | 4/2015 | Tan |
| 9,028,841 B2 | 5/2015 | Henn et al. |
| 9,131,884 B2 | 9/2015 | Holmes |
| 9,234,204 B2 | 1/2016 | Qvit-Raz et al. |
| 9,288,981 B2 | 3/2016 | Gandhi et al. |
| 2003/0031737 A1 | 2/2003 | Rosenbloom |
| 2003/0206995 A1 | 11/2003 | Bowling et al. |
| 2004/0053352 A1 | 3/2004 | Ouyang et al. |
| 2004/0096569 A1 | 5/2004 | Barkalow et al. |
| 2004/0115223 A1 | 6/2004 | Follansbee |
| 2004/0120991 A1 | 6/2004 | Schobel |
| 2004/0142463 A1 | 7/2004 | Walker et al. |
| 2004/0166501 A1 | 8/2004 | Azimzai et al. |
| 2004/0228804 A1 | 11/2004 | Jones et al. |
| 2005/0118655 A1 | 6/2005 | Weinstock et al. |
| 2005/0196358 A1 | 9/2005 | Georglades et al. |
| 2006/0035008 A1 | 2/2006 | Virgalli et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0207955 A1 | 9/2007 | Tanihara et al. |
| 2007/0218114 A1 | 9/2007 | Sorousch |
| 2007/0231923 A1 | 10/2007 | Cumberland et al. |
| 2008/0112983 A1 | 5/2008 | Bufe et al. |
| 2008/0267933 A1 | 10/2008 | Ohlson et al. |
| 2008/0305089 A1 | 12/2008 | Bufe et al. |
| 2009/0196907 A1 | 8/2009 | Bunick |
| 2009/0196908 A1 | 8/2009 | Lee |
| 2009/0205083 A1 | 8/2009 | Gupta et al. |
| 2010/0029832 A1 | 2/2010 | Pinnavaia et al. |
| 2010/0260720 A1 | 10/2010 | Sprenger |
| 2010/0285098 A1 | 11/2010 | Haley |
| 2011/0142942 A1 | 6/2011 | Gardner et al. |
| 2011/0217368 A1 | 9/2011 | Prakash et al. |
| 2012/0027786 A1 | 2/2012 | Gupta |
| 2012/0029832 A1 | 2/2012 | Dodgson |
| 2012/0039806 A1 | 2/2012 | Lahoud et al. |
| 2012/0058094 A1 | 3/2012 | Blasser et al. |
| 2012/0128597 A1 | 5/2012 | Peters et al. |
| 2012/0142548 A1 | 6/2012 | Corsi et al. |
| 2012/0276143 A1 | 11/2012 | O'Mahony et al. |
| 2012/0276525 A1 | 11/2012 | Kovarik et al. |
| 2013/0059815 A1 | 3/2013 | Fournell et al. |
| 2013/0157876 A1 | 6/2013 | Lynch et al. |
| 2013/0259834 A1 | 10/2013 | Klaenhammer et al. |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0330215 A1 | 12/2013 | Li |
| 2014/0044677 A1 | 2/2014 | Qvit-Raz et al. |
| 2014/0045744 A1 | 2/2014 | Gordon |
| 2014/0065209 A1 | 3/2014 | Putaala et al. |
| 2014/0065218 A1 | 3/2014 | Lang et al. |
| 2014/0066817 A1 | 3/2014 | Kovarik et al. |
| 2014/0068797 A1 | 3/2014 | Doudna et al. |
| 2014/0154290 A1 | 6/2014 | Peters et al. |
| 2014/0199266 A1 | 7/2014 | Park |
| 2014/0238411 A1 | 8/2014 | Kovarik |
| 2014/0255351 A1 | 9/2014 | Berstad et al. |
| 2014/0271867 A1 | 9/2014 | Myers |
| 2014/0333003 A1 | 11/2014 | Allen |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0377278 A1 | 12/2014 | Elinav et al. |
| 2015/0017227 A1 | 1/2015 | Kim |
| 2015/0064138 A1 | 3/2015 | Lu et al. |
| 2015/0071957 A1 | 3/2015 | Kelly |
| 2015/0086581 A1 | 3/2015 | Li et al. |
| 2015/0093473 A1 | 4/2015 | Barrangou |
| 2015/0132263 A1 | 5/2015 | Liu et al. |
| 2015/0150792 A1 | 6/2015 | Klingman |
| 2015/0166641 A1 | 6/2015 | Goodman |
| 2015/0190435 A1 | 7/2015 | Henn et al. |
| 2015/0216917 A1 | 8/2015 | Jones |
| 2015/0252358 A1 | 9/2015 | Maeder |
| 2015/0329555 A1 | 11/2015 | Liras |
| 2015/0329875 A1 | 11/2015 | Gregory |
| 2015/0352023 A1 | 12/2015 | Berg |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0008412 A1 | 1/2016 | Putaala et al. |
| 2016/0040216 A1 | 2/2016 | Wilder |
| 2016/0089315 A1 | 3/2016 | Kleinberg et al. |
| 2016/0089405 A1 | 3/2016 | Lue |
| 2016/0151427 A1 | 6/2016 | Whitlock et al. |
| 2016/0168594 A1 | 6/2016 | Zhang et al. |
| 2016/0206564 A1 | 7/2016 | Trachtman |
| 2016/0271189 A1 | 9/2016 | Cutcliffe |
| 2016/0314281 A1 | 10/2016 | Apte |

FOREIGN PATENT DOCUMENTS

| | | |
|---|---|---|
| WO | WO 2011/029701 | 5/2013 |
| WO | WO 2013/107750 | 7/2013 |

* cited by examiner

METHOD AND SYSTEM FOR REDUCING THE LIKELIHOOD OF DEVELOPING NASH IN AN INDIVIDUAL DIAGNOSED WITH NON-ALCOHOLIC FATTY LIVER DISEASE

RELATED APPLICATIONS

This application is a non-provisional of U.S. Provisional Patent Application Ser. No. 62/275,341, filed on Jan. 6, 2016.

This application is a continuation-in-part application of U.S. patent application Ser. No. 14/752,192 filed Jun. 26, 2015, which is a continuation-in-part application of U.S. patent application Ser. No. 14/225,503 filed Mar. 26, 2014, (now issued U.S. Pat. No. 9,445,936, issued Sep. 20, 2016), which is a continuation of U.S. patent application Ser. No. 13/367,052, filed Feb. 6, 2012 (now issued U.S. Pat. No. 8,701,671, issuing on Apr. 22, 2014), which claims priority of U.S. Provisional Patent Application Ser. No. 61/439,652, filed on Feb. 4, 2011 and U.S. Provisional Patent Application Ser. No. 61/556,023, filed on Nov. 4, 2011.

This application also is a continuation-in-part application of U.S. patent application Ser. No. 15/270,034, filed Sep. 20, 2016, which is a continuation-in-part application of U.S. patent application Ser. No. 14/954,074, filed on Nov. 30, 2015 (now issued U.S. Pat. No. 9,457,077, issuing on Oct. 4, 2016), which is a continuation-in-part application of U.S. patent application Ser. No. 14/574,517, filed on Dec. 18, 2014 (now issued U.S. Pat. No. 9,408,880, issuing on Aug. 9, 2016), which claims priority of U.S. Provisional Patent Application Ser. Nos. 62/072,476, filed on Oct. 30, 2014; 62/053,926, filed on Sep. 23, 2014; 62/014,855, filed on Jun. 20, 2014; and 61/919,297, filed on Dec. 20, 2013.

This application is also a continuation-in-part application of U.S. patent application Ser. No. 15/228,454, filed Aug. 4, 2016.

This application claims priority of U.S. Provisional Patent Application Ser. No. 62/274,550 filed Jan. 4, 2016.

This application is also a continuation-in-part application of U.S. patent application Ser. No. 14/611,458, filed Feb. 2, 2015, which is a continuation-in-part application of U.S. patent application Ser. No. 14/502,097, filed Sep. 30, 2014 (now issued U.S. Pat. No. 9,010,340, issuing on Apr. 21, 2015), which is a continuation of U.S. patent application Ser. No. 14/307,651, filed on Jun. 18, 2014 (now issued U.S. Pat. No. 8,936,030, issuing Jan. 20, 2015), which is a continuation-in-part application of U.S. patent application Ser. No. 14/079,054, filed Nov. 13, 2013 (now issued U.S. Pat. No. 8,757,173, issuing on Jun. 24, 2014), which is a continuation of U.S. patent application Ser. No. 13/425,913, filed Mar. 21, 2012 (now issued U.S. Pat. No. 8,584,685, issuing on Nov. 19, 2013), and claims priority of U.S. Provisional Patent Application Ser. No. 61/467,767, filed Mar. 25, 2011.

The entire disclosure of the prior applications are considered to be part of the disclosure of the accompanying application and are hereby incorporated by reference.

FIELD OF THE INVENTION

A method and system for treating non-alcoholic fatty liver disease (NAFLD) involves the modulation of the gut microbial of a person suffering from NAFLD, and in particular the provision of a probiotic therapy configured to reduce liver aminotransferases, total-cholesterol, TNF-α and to improve insulin resistance in NAFLD patients.

BACKGROUND OF THE INVENTION

NAFLD is the new pandemic of the twenty first century, co-existing with obesity. Fatty liver is caused by an abnormality in liver metabolism that results in the accumulation of fat. It can be seen as a consequence of metabolic deregulation associated with energy surplus and exceeded reservoir ability of adipose tissue to store fat/energy. NAFLD is strongly associated with obesity, insulin resistance (IR)/type 2 diabetes mellitus (T2DM) and the metabolic syndrome. Obesity, particularly central obesity, is highly predictive of hepatic steatosis and disease progression, being directly proportional to the increase of body mass index (BMI). More than two third of patients with type-2 diabetes have NAFLD.

NAFLD is also associated with increased overall mortality and particularly increased cardiovascular mortality. It is increasing worldwide, paralleling the obesity pandemic. It has been estimated that about one billion individuals worldwide have NAFLD. In the Western and in the Asian world, one third of the population is affected. NAFLD is presently the third cause of liver transplantation in the United States and is increasing at a rate such that it will be the first cause in the next few years.

NAFLD is the most common liver complication of irritable bowel syndrome and also affects people with ulcerative colitis and Crohn's disease. NAFLD has become the leading cause of chronic liver diseases worldwide, causing considerable liver-related mortality and morbidity. During the past decade, it has also become increasingly evident that NAFLD is a multisystem disease that affects many extra-hepatic organ systems, including the heart and the vascular system.

Non-alcoholic fatty liver disease is a condition ranging from benign lipid accumulation in the liver (steatosis) to steatosis combined with inflammation. The latter is referred to as non-alcoholic steatohepatitis (NASH). NASH is viewed as the hepatic component of metabolic syndrome. Estimates from the USA are that 5.7% to 17% of all adults have NASH, while 17% to 33% of Americans have NAFLD. As obesity and insulin resistance reach epidemic proportions in industrialized countries, the prevalence of both NAFLD and NASH is increasing and is therefore considered to be a major health hazard. Steatosis alone is considered a relatively benign condition for the liver itself and is also a reversible condition. However, the transition towards NASH represents a key step in the pathogenesis, as it sets the stage for further damage to the liver, such as fibrosis, cirrhosis and liver cancer. While the mechanisms leading to steatosis are well described, little is known about the actual risk factors that drive hepatic inflammation during the progression to NASH. Consequently, therapeutic options are poor.

The number one cause of death in patients with NAFLD is cardiovascular disease, followed by malignancies and then liver disease. Despite huge amounts of money spent on investigating its origins and prevention, there is presently no effective treatment for NAFLD. There is no clear curative treatment for NAFLD and thus, the management of patients is directed to controlling of co-morbidities known to promote not only liver disease, but also cardiovascular disease and overall mortality. At present, individuals diagnosed with NAFLD are treated by focusing on diet and exercise, in order to lose weight. Weight loss of 5% or more of body weight results in a NAFLD remission rate of 75%. In addition, recommendations are to have cholesterol intake lowered to 200 mg per day, whole grains emphasized and high fructose corn syrup avoided. Higher fructose consumption, in the form of soft drinks, has been associated with NAFLD as it is believed to promote bacterial overgrowth and hence increases the load of endotoxin that reaches the liver. Some studies have shown a possible beneficial effect in NAFLD for very mild alcohol consumption. Coffee has also been shown to have a protective effect in terms of metabolic control and NAFLD development and progression. The effect of lipid lowering agents in NAFLD is still not completely understood, though some studies have suggested a mild benefit in the use of statins. The accumulation of specific lipid intermediates, including DAG, acyl-CoA, and ceramide is thought to drive the progression of NAFLD in humans.

Existing treatments for NAFLD demonstrate various deficiencies. For example, available drugs such as vitamin E, pioglitazone, and pentoxifylline have borderline efficacy, but are limited by potential side-effects and toxicities, and do not improve liver fibrosis. Weight gain is common in patients taking thiazolidinediones, and these drugs can cause fluid retention and precipitate congestive heart failure. Rosiglitazone use is also associated with increased risk of myocardial infarction.

A genetic link to NAFLD has been studied but has not been found. NAFLD is more frequent in East Asian Indians, followed by Hispanics, Asians, Caucasians and less frequent in African Americans. While such racial disparities are not fully understood, it is known that African Americans have lower fructose absorption rates than Hispanics, and fructose is considered an important driver of liver steatogenesis.

The gastrointestinal tract harbors an abundant and diverse microbial community. It is a complex system, providing an environment or niche for a community of many different species or organisms, including diverse strains of bacteria. Hundreds of different species may form a commensal community in the GI tract in a healthy person, and this complement of organisms evolves from the time of birth to ultimately form a functionally mature microbial population.

A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of 'dysbiosis' or disrupted symbiosis, microbiota functions can be lost or deranged, resulting in increased susceptibility to pathogens, altered metabolic profiles, or induction of proinflammatory signals that can result in local or systemic inflammation or autoimmunity.

Long-chain-length hydrophobic acyl residues play a vital role in a multitude of essential biological structures and processes. Amongst other functions, they build the inner hydrophobic layers of biological membranes, are converted to intracellular storage compounds, and are used to modify protein properties or function as membrane anchors. Metabolic syndrome is an ever-increasing health problem among the world's population. It is a group of intertwined maladies that includes obesity, hypertriglyceridemia, hypertension, nonalcoholic fatty liver disease and diabetes mellitus type II (T2D).

There is a long felt but unsolved need for an effective treatment for NAFLD and the present invention is directed to a solution for this chronic and expanding disease.

SUMMARY OF THE INVENTION

One aspect of the present invention relates to the use of various *Lactobacillus* species to reduce LDL, cholesterol, and triglycerides to cause an improvement and amelioration of inflammation and steatosis. The present inventors believe that particular modulation of the gut microbiome, including the establishment and maintenance of certain beneficial bacteria, including *Lactobacillus, Bifidobacterium*, and certain *Streptococcus* species, forms the basis of a treatment of NAFLD, as well as NASH, and in particular, the use of particular species that have been modified via a CRISPR system. Nonalcoholic steatohepatitis (NASH) is a more advanced form of NAFLD where liver injury has occurred, and can lead to liver failure, portal hypertension, hepatocarcinoma and cirrhosis. Even without significant changes in BMI, glucose, or LDL2, probiotic use is believed to significantly decrease ALT, AST, total cholesterol, HDL, and TNF-α1.

Thus, in various embodiments of the present invention, the employment of particular probiotics as described herein, provides a treatment for NAFLD that shows improvements in intestinal dysbiosis, leading to decreasing intestinal permeability, endotoxemia and subsequent inflammation.

The most frequent cause which leads to obesity is a dysbalance between energy intake and energy expenditure. The gut microbiota contributes to host metabolism. Gut microbiota not only influence absorption and disposal of nutrients to the liver, but also can lead to the development of "metabolic endotoxemia" and activation of TLR ligands, which can stimulate liver cells to produce proinflammatory cytokines, thereby initiating inflammation and fibrogenesis, which characterize NASH. Another possible molecular mechanism implicated in NAFLD development is the alteration in LPS-endocannabinoid (eCB) system regulatory loops and bile acid metabolism. Thus, certain embodiments of the present invention are directed to the modification of intestinal bacterial flora by specific probiotics to achieve a therapeutic approach for the treatment of NAFLD.

One strategy for NAFLD treatment encompassed by the present invention relates to a treatment for obesity that involves manipulation of an individual's gut microbiota. Thus, modulation of gut microbiota by probiotic treatment or dietary intervention provides beneficial effects with respect to body weight, influence on glucose and fat metabolism, insulin sensitivity and reduction in chronic systemic inflammation, all of which can impact the status of NAFLD. Probiotic positive effects on host metabolism are specifically directed to beneficial levels of *Lactobacillus* and/or *Bifidobacterium* strains. For example, employment of *Saccharomyces cerevisiae* var. *boulardii, Enterobacter halii* or *Akkermansia muciniphila* are used to achieve beneficial effects for obesity and NAFLD. In certain embodiments, because obstructive sleep apnea and attendant fatigue are common in patients with NAFLD, one aspect of the present invention relates to the use of "no-snore strips" as described herein (and in more extensive pending patent applications incorporated herein by this reference, e.g. U.S. Pat. No. 9,445, 936) such that use of such strips can beneficially modify not only the populations of oral bacteria, but also snoring patterns, thus providing those suffering from NAFLD with a way to manage such condition to permit them to address fatigue issues and to thus sleep better, exercise more, etc.

Gut bacteria alter the way individuals store fat, how levels of glucose are balanced in the blood, and how humans respond to hormones that make individuals feel hungry or full. Certain population mixes of microbes set the stage for NAFLD, obesity and diabetes. The gut community in lean people is diverse while obese people have a gut microbe community that is comparatively less diverse. Lean individuals, for example, tended to have a wider variety of Bacteroidetes, a population of varied microbes that specialize in breaking down bulky plant starches and fibers into shorter molecules that the body can use as a source of energy.

Probiotics have physiologic functions that contribute to the health of gut microbiota, can affect food intake and appetite, body weight and composition and metabolic functions through gastrointestinal pathways and the modulation of the gut bacterial community. Thus, in various embodiments of the present invention, probiotics are employed, e.g. (*Enterococcus faecium, Streptococcus thermophilus L. acidophilus, Bifidobacterium longum, L. plantarum* and/or *B. lactis*) to significantly reduce total serum cholesterol and LDL cholesterol and to improve the LDL:HDL cholesterol ratio. In particular embodiments, a CRISPR-Cas system (Clustered Regularly Interspaced Short Palindromic Repeats-CRISPR-associated) is employed to alter one or more of these bacteria to modify various virulence factors associated with bacteria so that beneficial populations of bacteria inhabit an individual's oral and/or gut microbiome.

Various embodiments of the present invention relate to a composition capable of increasing the level of anti-oxidized low-density-lipoprotein (oxLDL) antibodies in vivo for use in the treatment or prevention of NASH. OxLDL is an immunogenic molecule that stimulates the induction of anti-oxLDL antibodies. Phosphorylcholine, a component of *Streptococcus pneumoniae*, is a major antigen in oxLDL, which is recognized by anti-oxLDL antibodies that have protective properties. One embodiment relates to the expression of OxLDL in bacteria via employment of a CRISPR-Cas system to insert genes for OxLDL such that such modified bacteria produce OxLDL to therefore stimulate the induction of anti-oxLDL antibodies, thus providing the protective effects of such antibodies. Using the present invention, fibrosis can be decreased or prevented by the production and administration of anti-oxLDL antibodies to avoid inflammation of the liver and to therefore treat NASH and NAFLD. While antibodies against oxLDL are known in the art, various embodiments of the present invention relate to a new medical use of such antibodies, as well as to methods and systems that modify gut bacteria to enhance the production of such antibodies. In other words, various embodiments of the invention relate to a composition comprising antibodies against oxLDL for use in the treatment or prevention of hepatic inflammation or more in particular the treatment or prevention of NASH, and/or the use of oxLDL antibodies for the preparation of a medicament for the treatment or prevention of hepatic inflammation and in the treatment of NASH. In certain embodiments, a method of treatment or prevention of hepatic inflammation is provided where oxLDL antibody levels are increased by modification of particular bacteria using a Clustered Regularly Interspaced Short Palindromic Repeats-CRISPR-associated system (CRISPR-Cas) or Clustered Regularly Interspaced Short Palindromic Repeats from *Prevotella* and *Francisella* 1 (CRISPR/Cpf1) system so that the bacteria is able to produce desired levels of oxLDL anti-bodies.

In other embodiments, the methods and systems disclosed herein are directed to modifying the gut microbiota of an individual to ameliorate the progression of NAFLD, including reducing liver aminotransferases, total-cholesterol, TNF-α and improving insulin resistance in individuals with NAFLD. In certain embodiments, NAFLD is thus treated by modulation of the gut microbiota. Effective treatments include employing a method of populating a subject's gastrointestinal tract with a diverse and useful selection of microbiota in order to alter a dysbiosis. Various aspects and embodiments of the invention are directed to methods and compositions for modulation of NAFLD of an individual's gut microbiome by using bacteria that have been treated with a CRISPR-Cas or CRISPR-Cpf1 system to reverse antibiotic resistance or to render ineffective certain virulence factors in pathogenic bacterial cell, as well as modifying gut bacteria in a manner to make them "better" in various ways, including an ability to outcompete other undesired bacteria. Other various embodiments of the present invention relate to the employment of engineered autonomously distributed circuits containing programmable nucleases (e.g. "programmable nuclease circuits") that are delivered to microbial organisms in vivo to modulate the expression of certain antibiotic resistant and virulence factors of particular microbial organisms. Some embodiments employ the Type II CRISPR-Cas (Clustered Regularly Interspaced Short Palindromic Repeats-CRISPR-associated) system of *Streptococcus pyogenes* to reverse antibiotic resistance in a wide range of microbial organisms. In certain embodiments, the CRISPR-Cas system is used to weaken resistance of microbial pathogens to existing antibiotics. The use of the CRISPR-Cas system may be viewed as a paradigm shift in combating pathogens because it enables autonomous and distributed neutralization of disease at the gene level. Various aspects of the present disclosure provide methods that comprise modifying bacterial cells to target a gene or nucleotide sequence of interest, and in particular, genes involved in the storage of fat. Such modified bacterial cells include an engineered autonomously distributed circuit having at least one nucleic acid encoding a programmable nuclease that targets a gene or nucleotide sequence directed to fat metabolism.

While there are medications approved for treating diseases and conditions associated with NAFLD, there are currently no medications specifically approved for the treatment of NAFLD itself. Treatment protocols have instead been focused upon the associated conditions, such as the metabolic syndrome. Conventional treatment of NAFLD includes weight loss, restricting dietary fat, administration of medications employed in the treatment of an associated condition and administration of medications employed in the treatment of hyperlipidemia. Many medications employed to treat conditions associated with NAFLD are hepatotoxic.

Various embodiments of the present invention are directed to a method for treating NAFLD in a subject in need thereof that includes administering a composition including a therapeutically effective amount of *Prevotella*, and more preferably *Prevotella* that has been modified, e.g. by CRISPR-Cas, in a manner that reduces the effect of at least one of the virulence factors of such bacteria. Other embodiments involve the employment of bacteria of the *Bacteroides* family that have been modified to reduce the amount of a ligand-activated transcription factor.

Dysbiosis in a person's gut has a significant role in the pathogenesis of human NAFLD/NASH. In various embodiments of the present invention, administration of probiotics, as well as associated fiber diets to support such bacteria, is involved, in some embodiments employing *Bifidobacterium* and *Lactobacillus* strains. Control of the bacterial flora lowers proinflammatory cytokine production (tumor necrosis factor-α, interleukin-6, interferon-γ) via down-regulation of the nuclear factor kappa B, and decreases oxidative stress. Probiotics can reduce the urease activity of bacterial microflora, decrease fecal pH value and reduces amino-acid fermentation and ammonia adsorption; reduce aminotransferases, and improve the lipid status in NAFLD patients. Each of these may be modified via CRISPR-Cas systems employed to alternative characteristics of an individual's microbiome.

Microbiome research in liver disease has evolved recently as an exciting new field. Prebiotics encompass products that promote the growth of beneficial intestinal microbiota. Probiotics include live microbial strains in predefined quantities. Both prebiotics and the use of probiotics is involved in the various embodiments of the invention as herein described. The present invention is directed in various embodiments directed to ways to modify the microbiota to treat hepatic steatosis, liver inflammation, fibrosis, and developing and advanced liver disease. The purposeful manipulation of the gut microbiota is done to address various liver diseases at both early and late disease stages.

More than 90% of the adult microbiome is composed of species belonging to four bacterial phyla: Firmicutes, Bacteroidetes, Actinobacteria, and Proteobacteria. Differences exist, however, with respect to different individuals as well as in different habitats. For example, Firmicutes are the major species in the intestine, vagina, skin, and oral cavity, while Actinobacteria and Proteobacteria are more dominant in the oral cavity, skin, and nasal cavity. The enterotype is a classification of the microbiome, with the gut microbiome being classified into three enterotypes. Each enterotype includes a dominant species selected from the group consisting of: *Bacteroides, Prevotella*, and Ruminococcus, with enterotypes being unrelated to race, residential region, or diet.

The prevalence of nonalcoholic fatty liver disease (NAFLD) overall is lower in Asia than in Western countries. Urban areas in India and other parts of Asia that have adapted a 'Western' diet report prevalence rates for NAFLD and NASH of 10-24 and 3-4%, respectively, which is similar to their prevalence rates in the West. In addition, the prevalence of NAFLD in an obese population was similarly high in Asia and Western countries. Thus, differences in NAFLD etiology and prevalence are more closely related to dietary patterns than geographic differences.

It is believed that commensal microbiota protect against biliary injury and liver fibrosis. The present inventor believes that there is a significant association of fatty liver with *H. pylori* infection. Thus, various embodiments involve the modification of an individual's microbiome, including *H. pylori* in one's stomach, to combat NAFLD and NASH. Thus use of CRISPR-Cas to render *H. pylori* more susceptible to particular antibiotics is one way in which such modification may be achieved.

NAFLD is a complex disease and a treatment targeting one pathological process often also causes changes in other pathways. Prebiotics represent a specific type of dietary fiber that when fermented, mediate measurable changes within the gut microbiota composition, usually causing an increase in the relative abundance of bacteria thought of as beneficial, such as bifidobacteria or certain butyrate producers. Prebiotics are usually non-digestible carbohydrates, oligosaccharides or short polysaccharides, including inulin, oligofructose, galactofructose, galacto-oligosaccharides and xylo-oligosaccharides, all leading to increasing the relative abundance of bifidobacteria and lactobacilli. The gut of individuals with various maladies, including obesity, harbor bacteria in their gut that establishes an inflammation-associated microbiome, often providing a lower potential for butyrate production and reduced bacterial diversity. Thus, one objective of the present invention is to alter the microbiome of such individuals to increase bacterial diversity in their gut and to increase levels of butyrate production. Patients with NAFLD have small intestinal bacterial overgrowth and increased intestinal permeability. Thus, altering the microbiome of such individuals is achieved to counter the progression of NAFLD. In certain embodiments, one objective is to increase the proportion of Ruminococcaceae in a person's microbiome and to also reduce the proportion of *Escherichia*, e.g. by modifying *Escherichia* via CRISPR-Cas to make it less viable than it otherwise would be.

Probiotics can reduce liver aminotransferases, total cholesterol, tumor necrosis factor α and improve insulin resistance in patients with NAFLD. Similarly, treatment of other diseases in the gut, like inflammatory bowel disease (IBD) is implicated with respect to modification of the gut microbiome. The concept of an altered gut microbiota or dysbiosis is possibly the most significant development in IBD and NAFLD research in the past decade. A definitive change of the normal gut microbiota with a breakdown of host-microbial mutualism is believed to be the defining event in IBD and NAFLD development.

In other embodiments, one objective is to increase the levels of *Lactobacillus, Leuconostoc, Lactococcus, Pediococcus* and Firmicutes in an individual's gut microbiome, while reducing the levels of Bacteroidetes and *Akkermansia* spp. In certain other embodiments, one objective is to increase the levels of *Prevotella* and *Roseburia* (a butyrate-producer) in a person's gut microbiome, and especially the colon microbiome. Other embodiments focus on increasing the levels of *Bacteroides* in the person's gut and decreasing the levels of *Escherichia*, Lachnospiraceae and Megasphaera.

Periodontal disease is a chronic infectious disease of the tissues surrounding the teeth that result in tooth loss. Several reports have indicated that periodontal infection is related to NAFLD. Both NAFLD and periodontal disease are chronic inflammatory conditions that are known as 'silent diseases'. Therefore, both conditions need to be detected early and treated under collaborative medical and dental care in order to prevent progression to NASH. The prevalence of NAFLD in the American general adult population is 10%-40% and that of NASH is approximately 2%-5%. One aspect of the present invention is directed to the relationship between periodontal pathogens, e.g. composed of *P. gingivalis*, and the severity of NAFLD. The eradication of periodontal pathogens, such as *P. gingivalis* infection, is believed to have a beneficial effect upon NASH.

Certain embodiments of the present invention are directed to a method for treating non-alcoholic fatty liver disease by providing to an individual in need thereof an effective amount of a composition comprising modified *L. reuteri* bacteria, preferably using CRISPR-Cas and/or Cpf1 systems, to provide such bacteria in a manner so that they have the ability to survive the conditions in the duodenum or jejunum of the small intestine. Other embodiments involve a method for treating non-alcoholic fatty liver disease involving establishing in the gut of an individual a population of beneficial bacteria selected from the group consisting of *Lactobacillus, Bifidobacterium*, and *Streptococcus* species and administering at least 6 grams per day of fiber to the individual to maintain the beneficial bacteria in the gut of the individual. Still other embodiments are directed to a method for treating non-alcoholic fatty liver disease by increasing oxLDL antibody levels in an individual by modifying bacteria, preferably using a CRISPR-Cas or Cpf1 system, so that the bacteria is able to produce desired levels of oxLDL. Yet other methods involve the modulation of NAFLD of an individual's gut microbiome by using beneficial bacteria, e.g. such as one or more of bacteria from one or more of the phylas: Firmicutes, Bacteroidetes, Actinobacteria, and Proteobacteria, preferably treated with a CRISPR-Cas or CRISPR-Cpf1 system to reverse antibiotic resistance or to render ineffective certain virulence factors in pathogenic bacterial cells. In other embodiments, an individual is administered a therapeutically effective amount of *Pre*- votella, and more preferably *Prevotella* that has been modified in a manner that reduces the effect of at least one of the virulence factors of such bacteria. Certain embodiments are directed to a method for treating non-alcoholic fatty liver disease involving the modifying of bacteria of the *Bacteroides* family so that they produce reduced amounts of a ligand-activated transcription factor as compared to non-modified bacteria. In preferred embodiments, probiotics are further provided to feed such bacteria, with the result being improvements in levels of density lipoprotein, and tumor necrosis factor-α.

One will appreciate that this Summary of the Invention is not intended to be all encompassing one of skill in the art will appreciate that the entire disclosure, as well as the incorporated references, provides a basis for the scope of the present invention as it may be claimed now and in future applications.

DETAILED DESCRIPTION OF PREFERRED EMBODIMENTS

Figure 1:
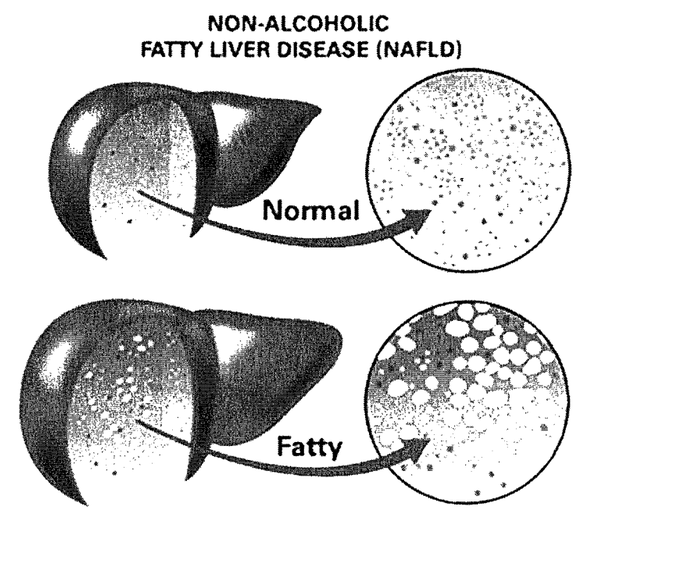
FIG. 1 is an illustration depicting the visual difference in appearance between a normal liver and a liver with non-alcoholic fatty liver disease.

Probiotic therapies can reduce liver aminotransferases, total-cholesterol, TNF-α and improve insulin resistance in NAFLD patients. Modulation of the gut microbiota represents a new treatment for NAFLD. In certain embodiments, the methods and systems as described herein are directed to inhibiting glucosphingolipid synthesis in an individual by provision of particular microbes effective to achieve such inhibition. In other embodiments, an engineered autonomously distributed circuit that contains a programmable nuclease able to target a virulence factor or an antibiotic resistance gene of the bacterial species is employed, whether they be Gram-negative bacterial cells, Gram-positive bacterial cells, or a combination thereof. Microbial cells may include members of the phyla Actinobacteria, Bacteroidetes, Proteobacteria, Firmicutes, or a combination thereof. In particular embodiments, gut bacteria are modified to address the synthesis of triacylglycerol. There is a direct correlation between high triacylglycerol (triglyceride; TAG) levels and the severity of metabolic syndrome. Thus, controlling the synthesis of TAG will have a great impact on overall systemic lipid metabolism and thus metabolic syndrome progression.

The Acyl-CoA: monoacylglycerolacyltransferase (MGAT) family has three members (MGAT1, -2, and -3) that catalyze the first step in TAG production, conversion of monoacylglycerol (MAG) to diacylglycerol (DAG). TAG is then directly synthesized from DAG by a Acyl-CoA: diacylglycerolacyltransferase (DGAT). The conversion of MAG→DAG→TAG is the major pathway for the production of TAG in the small intestine, and produces TAG to a lesser extent in the liver.

One aspect of various embodiments of the present invention is directed towards the therapeutic potential of inhibiting MGAT for lowering TAG synthesis. Elevated plasma TAG has been associated with an increased risk of coronary and cerebrovascular ischemic events. Excessive TAG synthesis in the intestine due to dietary fat absorption followed by increased accumulation of TAG in the liver and adipose plays an integral role in the progression of metabolic disorders including obesity, insulin resistance, T2D, and fatty liver disease. Limiting TAG production in humans provides a way to address these metabolic disorders.

TAG is de novo synthesized in the liver and adipose tissue, while dietary TAG is broken down and re-synthesized in the small intestine. In the liver, TAG is used for very low density lipoprotein (VLDL) assembly. Newly formed VLDL is secreted into the circulatory system where it transports neutral lipids including TAG to peripheral tissues. In the small intestine, dietary TAG is hydrolyzed by pancreatic lipase to FA and MAG that are re-absorbed in the intestinal lumen. Enterocytes then re-synthesize TAG and secrete it as ApoB-containing chylomicrons that deliver dietary fat to tissues. Most tissues including liver and adipose use the G3P pathway for the synthesis of TAG. In contrast, the small intestine predominately relies on the MAG pathway.

MGAT is a major regulator of TAG homeostasis in response to diet. In humans, the expression of MGATs is up-regulated in the livers of insulin-resistant patients who have nonalcoholic fatty liver disease (NAFLD). MGAT has related acyltransferases (DGAT) and they share similar molecular relationships, however, MGAT genes share homology with DGAT2 and not DGAT1. DGAT1 is mainly expressed in adipose and small intestine tissues; DGAT2 is expressed in liver tissue. There exists a fundamental role for DGAT2 in TAG biosynthesis, much more so than DGAT1.

There presently are very few therapeutics existing to treat NAFLD. Various aspects of the present invention relate to the inhibition of MGAT2 to lower TAGs and to also reduce or eliminate the progression of NAFLD, which ultimately progresses to NASH, and later cirrhosis. In certain embodiments, protection of the liver from developing NASH involves the inhibition of MGAT2 synthesis (rather than MGMAT1). Thus, various embodiments of the present invention are directed to the protection of the liver from developing NASH by effective inhibition of MGAT2 synthesis by employing bacteria of an individual's microbiome, especially using bacteria modified via CRISPR-Cas systems to achieve inhibition of MGAT2 synthesis.

In still other embodiments, protection of the liver from developing NASH involves the inhibition of MGAT3 synthesis. The MGAT3 gene, Mogat3, exists only in higher mammals and not in rodents. Thus, employment of bacterial systems, especially engineered gut microbes that carry inhibitors of Mogat3, is one method and system to achieve the treatment, likelihood of prevention and the prevention of NAFLD. The sequence of MGAT3 is more homologous to DGAT2 than to MGAT1 or MGAT2. Thus, MGAT3 exhibits significantly higher DGAT activity than MGAT1 and MGAT2. MGAT3 expression levels increase in patients with NAFLD and its levels decrease after gastric bypass surgery-induced weight loss. It is therefore believed that MGAT3 plays a more important role than MGAT2 in obesity related hepatic insulin resistance and NAFLD progression in humans. In various embodiments of the present invention either the expression of MGAT2 or MGAT3, or both, is employed to combat NAFLD, and in particular, via the employment of modified gut bacteria via enhancement of such expression by use of the CRISPR-Cas/Cpf1 systems as described herein.

While the inhibition of human intestinal DGAT enzyme blocks TAG synthesis completely and has led to severe fat malabsorption, the use of DGAT1 inhibitors as anti-diabetes and/or anti-obesity agents is not favored due to gastrointestinal side effects. One aspect of the present invention is directed to achieving the reduction of TAG synthesis without these gastrointestinal side effects.

In human liver tissue, MGAT2/MGAT3 expression is correlated with the progression of NAFLD. In the small intestine, MGAT2 inhibition results in changes in TAG absorption and synthesis, as well as incretin secretion. These actions contribute to weight loss, improvement of insulin sensitivity and hypertriglyceridemia, and the prevention of NAFLD progression. While the blocking of dietary TAG absorption using inhibitors to DGAT1 exhibit unwanted gastrointestinal side effects, the targeting of the MAG pathway as a therapeutic for metabolic syndrome is a viable option for inhibiting intestinal TAG synthesis without such side effects. Inhibition of intestinal MGAT2 results in dynamic changes in TAG and cholesterol absorption, which leads to the changes in systemic energy balance and gut incretin release. Inhibition of the MGAT2 isozyme in the liver improves steatosis by attenuating fat accumulation and insulin resistance. In adipose, MGAT2 inhibition reduces fat biosynthesis and improves glucose uptake. Thus, one aspect of the present invention relates to either or both MGAT3 and MGAT2 inactivation in various tissues, especially by employing modified gut bacteria as described herein, to achieve the benefits of reducing body weight, improving insulin resistance, decreasing hyperlipidemia, and attenuating hepatic steatosis.

Acyl-CaA:diacylglycerol acyltransferase (DGAT) catalyzes the final step in triglyceride synthesis by facilitating the linkage of sn-1,2 diacylglygerol (DAG) with a long chain acyl CoA. There are two primary isoforms of DGAT, DGAT-1 and DGAT-2. DGAT-1 is primarily expressed in the small intestine while DGAT-2 exhibits primarily hepatic expression where its expression is insulin responsive. Inhibiting expression of DGAT-2 significantly improves hepatic steatosis. Thus, the materials and methods of various embodiments of the present invention can be used to alter expression of DGAT-2 for the treatment of NASH and NALFD, and to reduce hepatic insulin resistance. While certain aspects of the present invention can involve the use of engineered nucleases to knock out DGAT-2 in a subset of liver cells, or involve the use of an engineered transcription factor that can be used to down-regulate DGAT-2 expression, other more preferred treatment methods employ the use of CRISPR-Cas or Cpf1 systems to inhibit DGAT-2 expression.

In still other embodiments, the present invention is directed to addressing primary sclerosing cholangitis (PSC), a disease that involves severe inflammation and scarring that develops in the bile ducts and is associated with patients who suffer from IBD. Those with PSC may ultimately require liver transplantation. The cause is not known and there is no effective medication for PSC. Primary biliary cirrhosis is a chronic inflammatory intrahepatic liver disorder that slowly destroys the small-to-medium-sized bile ducts within the liver. When these ducts are damaged, bile builds up in the liver (cholestasis) and over time damages liver tissue. Primary sclerosing cholangitis is a similar, but affects the part of the bile duct that is outside of the liver. In both diseases, inflammation leads to progressive thickening, scarring, and destruction of the bile ducts. The buildup of bile, bile salts, and cholesterol in the liver causes damage to cell membranes in the liver, reduced production of bile salts, and fibrosis (development of scar tissue). Fibrosis is both a marker of liver damage and a potential contributor to liver failure. Continuing damage causes scarring or cirrhosis of the liver (the liver slowly deteriorates and malfunctions), and prevents proper liver function and impaired blood circulation in the intestines. While not bound by theory, these diseases are believed to be autoimmune diseases and the present inventor believes that modulation of a person's gut microbiota can avoid the development of such autoimmunity, thus providing a treatment and method of preventing PBC and PSC. It is believed that bacterial antigens translocate across a leaky and possibly inflamed gut wall into the portal and biliary system to induce an abnormal immune response and contribute to primary sclerosing cholangitis pathogenesis.

In various embodiments, the focus of modification of an individual's microbiome is directed to the microbiome of the small intestine, while in others it is directed to the colon, and in still others, to both. One strategy in the treatment of NAFLD is to ameliorate or turn off inflammatory triggers, with some of the main targets including cytokines such as tumor necrosis factor (TNF)-α, chemokines, TLR4, and the NLRP3 inflammasome. Gut microorganism-derived bacterial products including endotoxin (lipopolysaccharide), peptidoglycan, and bacterial DNA can travel up the portal vein to activate TLR4 and TLR9 on Kupffer cells and other hepatic cell types. In turn, this activation can lead to the release of cytokines and chemokines that promote NASH. In still other embodiments, modulation of particular bacteria by CRISPR-Cas and Cpf1 systems, for example, to address bacterial pyruvate dehydrogenase complex component E2 (PDC-E2) homologues in particular bacteria, including but not limited to *E. coli, Novosphingobium aromaticivorans, Mycobacterium* and *Lactobacillus* species, are used to effectively treat and/or prevent these diseases. There is believed to be a common core gut microbial response to chronic inflammation and immune activation, such as observed in type 2 diabetes.

In yet other embodiments of the present invention, the present inventors submit that bacterial expression of RNA molecules can be employed to generate miRNA molecules that interact with the human host mRNA during bacterial infection. Thus, such micro-RNAs derived from bacterial RNAs are used to regulate gene expression of the human host cell involved in different human diseases, including NAFLD. Bacterially derived microRNA sequences can significantly regulate the expression of various human genes and thus, enhancing an individual's gut bacteria by employing CRISPR systems to regulate microRNA sequences forms various embodiments of the present invention. In addition to NAFLD, microRNAs are believed to be involved in many human diseases, such as cancer, diabetes, rheumatoid arthritis, and others that respond to a particular bacterial environment, and thus, while the present description is focused on NAFLD, it will be understood that other diseases can similarly be addressed by employment of the systems and methods as described herein.

MicroRNAs (miRNA) are small important regulators of gene expression and are currently believed to regulate approximately 70% of human genes. More than a thousand different miRNA have been characterized in the human genome and they all are assumed to function by a similar mechanism: The miRNAs base-pair with target messenger RNA (mRNA) and recruit nucleases that degrade the targeted RNA from the termini and/or inhibit translation. In cancer and many other diseases, deregulation of gene-expression is observed and in many cases miRNAs have been shown to play an integral part or even the causative role in disease development. According to various embodiments, the present invention concerns a method for the treatment, amelioration or prevention of a disease or medical disorder associated with the presence or over-expression of micro- RNA. Therefore, in certain aspects of the invention, inhibiting miRNA activity is a strategy to treat disease, especially NAFLD.

miRNAs are a class of highly conserved non-coding regulatory factors that negatively regulate more than half of the protein-coding genes in mammals, are essential to most biological processes, including proliferation, differentiation and apoptosis, and their transcription is tightly controlled. In certain embodiments, a CRISPR system and/or a modified CRISPR interference system (CRISPRi) employing inactive Cas9, may be used to reversibly prevent the expression of both monocistronic miRNAs and polycistronic miRNA clusters. Such CRISPR-based systems are reversible and thus provide advantages over more conventional knockdown techniques. The CRISPR/CRISPRi system may be adapted to target a particular miRNA sequence by employing a single repression vector, often entailing using a 20-bp sequence and thus, such a CRISPR/CRISPRi method is useful in the generation of vectors that target multiple miRNAs and with reduced toxicity and can silence miRNAs with no off-target effects. Using such CRISPR systems to silence miRNAs involved in the progression of NAFLD is therefore one focus of particular embodiments of the present invention.

In various embodiments, particular bacterial species are targeted for modification and use to address the treatment of NAFLD. For example, *L. reuteri* is well-established as one of the most ubiquitous members of the naturally-occurring gut bacteria. Host-specific strains of *L. reuteri* have been documented to confer broad-spectrum protection from an assortment of microbial and chemical associated disease in humans and animals. However, traditional probiotic therapy involves administration of bacteria with the hope that some bacteria will survive the harsh gastric conditions and colonize the colon where the bacteria will reproduce and live indefinitely. Far fewer bacteria survive in the duodenum, jejunum or ileum because of factors such as acidity, immune response and bile concentration. In certain embodiments, it is believed that bacteria must be present in the duodenum or jejunum of the small intestine for lowering cholesterol and in particular bile acid. Thus, certain aspects of the present invention are directed to the modification of particular bacteria using CRISPR-Cas and/or Cpf1 systems to provide bacteria having the ability to survive the conditions in the duodenum or jejunum of the small intestine. Thus, in one embodiment, CRISPR systems are employed to render certain bacteria adaptive to harsh acid conditions and that are otherwise considered to be beneficial to a person in avoiding fatty liver disease. Highly bile salt hydrolase active bacteria provide an improved agent for reducing serum cholesterol, serum lipids, body fat, and atherogenic index and for prophylaxis and treatment of atherosclerosis, cardiovascular and cerebrovascular diseases. Modification of an individual's gut microbes to render a significant population thereof to have enhanced degrees of BSH characteristics is one objective of various embodiments of the present invention.

Oral administration of probiotics has been shown to significantly reduce cholesterol levels, such cholesterol-lowering effects ascribed to BSH activity. Deconjugated bile salts are less efficiently reabsorbed than their conjugated counterparts, which results in the excretion of larger amounts of free bile acids in feces. Also, free bile salts are less efficient in the solubilization and absorption of lipids in the gut. Therefore, deconjugation of bile salts is believed to lead to a reduction in serum cholesterol either by increasing the demand for cholesterol for de novo synthesis of bile acids to replace those lost in feces or by reducing cholesterol solubility and thereby absorption of cholesterol through the intestinal lumen. Microbial BSHs function in the detoxification of bile salts and in doing so increase the intestinal survival and persistence of producing strains. Thus, one embodiment of the present invention is directed to enhancing the BSH activity by a probiotic bacterium to maximize its prospects of survival in the hostile environment of the gastrointestinal tract. Increased intestinal survival increases the overall beneficial effects associated with strains possessing such BSH enhanced activities. Enhanced BSH activity benefits probiotic bacterium that are able to survive and perform in the intestinal milieu. BSH significantly contributes to bile tolerance and survival and persistence of strains in the intestinal tract. Thus, certain embodiments are directed to the manipulation of bacterial strains to enhance the BSH activity of probiotic strains (either to over express a native BSH or to express or over express a heterologous BSH) to improve their survivability in the intestinal tract. Extraction of fecal bacteria form a person and employing the techniques as described herein on such native populations to enhance various aspects thereof, including for example BSH activity, and then returning such modified gut bacteria to the individual, is one method that may be used to address NAFLD in a positive manner.

This is accomplished in various embodiments by the employment of CRISPR-Cas and Cpf1 systems to insert BSH genes in select bacteria. Certain embodiments include the administration of bile-hydrolyzing strains (especially those modified by CRISPR-Cas and/or Cpf1 systems) to control serum cholesterol. The ingestion of probiotics as described herein is believed to be deemed preferable to statins as a way to achieve a cholesterol-lowering therapy. Manipulation of BSH activity as described herein provides for more robust probiotics (whether delivered orally or via the fecal transplantations as described herein) with improved competitiveness and performance. Statin drugs target many of the underlying inflammatory pathways involved in metabolic syndrome (MetS). Thus, certain embodiments relate to the use of CRISPR-Cas systems to modify bacteria of an individual's microbiome so that they produce effective levels of statin drugs. The metabolic syndrome (MetS) is comprised of a cluster of closely related risk factors, including visceral adiposity, insulin resistance, hypertension, high triglyceride, and low high-density lipoprotein cholesterol; all of which increase the risk for the development of type 2 diabetes and cardiovascular disease. A chronic state of inflammation appears to be a central mechanism underlying the pathophysiology of insulin resistance and MetS. Thus in various embodiments of the present invention, use of probiotics and prebiotics in combination, as described herein, is employed to address the cause of NAFLD, but that is also believed to address related conditions, such as MetS.

In one embodiment, the bacteria employed and that are modified via CRISPR-Cas and Cpf1 to enhance expression of BSH include *Lactobacillus, Bifidobacteria, Pediococcus, Streptococcus, Enterococcus*, or *Leuconostoc*. In another embodiment, the *Lactobacillus* is *Lactobacillus reuteri*, optionally, *Lactobacillus reuteri* (NCIMB 701359), *Lactobacillus reuteri* (NCIMB 701089), *Lactobacillus reuteri* (ATCC 55148), *Lactobacillus reuteri* (ATCC 23272), *Lactobacillus reuteri* (NCIMB 702655), *Lactobacillus reuteri* (LMG 18238), *Lactobacillus reuteri* (CCUG 32271), *Lactobacillus reuteri* (CCUG 32305), *Lactobacillus reuteri* (CCUG 37470), *Lactobacillus reuteri* (CCUG 44001) or *Lactobacillus reuteri* (CCUG 44144). In another embodiment, the *Lactobacillus reuteri* adheres to the gastrointestinal epithelial cells, competes for adhesion, or inhibits the binding of other bacteria due to cell surface proteins.

The human gut is a rich habitat populated by numerous microorganisms, each having a CRISPR system. In certain embodiments, the CRISPR-Cas system may be employed to render certain bacteria sensitized to certain antibiotics such that specific chemical agents can selectively choose those bacteria more susceptible to antibiotics, see, e.g. US Pat. Publication No. 2013/0315869 to Qimron, which is incorporated in its entirety by this reference. Another aspect of certain embodiments includes making synthetic CRISPR-containing RNAs that target genes of interest and using them with Cas enzymes.

In various embodiments, the CRISPR-Cas and or Cpf1 system is employed to control the composition of the gut flora, such as by circumventing commonly transmitted modes of antibiotic resistance and distinguishing between beneficial and pathogenic bacteria. For applications that require the removal of more than one strain, multiple spacers that target shared or unique sequences may be encoded in a single CRISPR array and/or such arrays may be combined with a complete set of cas genes to instigate removal of strains lacking functional CRISPR-Cas/Cpf1 systems. Because of the sequence specificity of targeting, CRISPR-Cas/CPF1 systems may be used to distinguish strains separated by only a few base pairs.

There are ongoing ethical concerns arising with respect to the use of CRISPR-Cas systems—especially as it relates to modification of the human genome. In preferred embodiments of the present invention, however, such issues are much less prevalent for various reasons. First, because preferred embodiments relate to the modification of microbes—rather than to the human genome—and especially those microbes that show tropism for humans, the unintended consequences of employing Crispr-Cas on organisms is lessened, if not eliminated. Moreover, use of CRISPR-Cas to also insert genes that have controllable elements such that the cells are killed by triggering the expression of such genes, is another way to reduce if not eliminate concerns about an unintended release of a modified organism. These types of controls are well known to those of skill in the art and have been long employed, for example, by those involved in creating genetically engineered organisms, such as by inserting genes so that organisms become susceptible to various conditions, such as temperature, antibiotic exposure, etc., such that microbes that may somehow escape desired conditions will not be viable. Modifying the human genome, made possible by the CRISPR technique, has its upsides but also equally daunting downsides. Permanent deletion of genes from the human genome is much more controversial than deletion or modification of bacterial genes. Thus, one desirable aspect of the present invention is directed to the far less controversial modification of gut microbes resident in the human being to promote health and to trigger the desired immune responses as described herein.

In other embodiments, the use of CRISPR-Cas systems is employed to increase butyrate production of select bacteria. For example, *F. prausnitzii*, one of the most abundant species in the colon, is an important producer of butyrate, a major product of carbohydrate fermentation which is implicated in providing protection against colorectal cancer and ulcerative colitis. CRISPR systems are used to enhance the production of butyrate by insertion of genes into select *F. prausnitzii* bacteria to protect against colorectal cancer and other diseases.

Because CRISPR-Cas/Cpf1 acts before transcription occurs, it is able to be employed to target regulatory and other elements on the DNA of microbes that make up a person's gut microbiome. In certain embodiments, CRISPR-Cas may be employed to deliver fluorescent markers to certain DNA sequences, thus permitting one to determine whether any particular sample has been treated in accordance with the present invention, thus ensuring, for example, identity of various materials, compliance with safety issues, effectiveness of gene expression or excision, etc. permitting labeling of living cells with a desired color to discern particular attributes and states.

Other embodiments are focused on diet as it relates to the use of probiotics. The gut microbiota plays a critical role in transforming dietary polyphenols into absorbable biologically active species, acting on the estimated 95% of dietary polyphenols that reach the colon. Certain embodiments rely upon the ability to deliver agents via mucosal adhesive strips, such as described, for example, in U.S. Pat. No. 8,701,671, which is fully incorporated herein by this reference. Thus, in various embodiments of the present invention, the engineering of communal bacteria with improved properties using a CRISPR/Cas system is employed to provide for the enhancement of health, especially as it relates to an individual's microbiome. In certain embodiments the present invention is directed to delivering to microbial cells in vivo a delivery vehicle with at least one nucleic acid encoding a gene or nucleotide sequence of interest, such method employing an RNA-guided nuclease. The microbial cells may be either or both pathogenic microbial cells or non-pathogenic bacterial cells and the gene or nucleotide sequence of interest may be a virulence factor gene, a toxin gene, an antibiotic resistance gene, or a modulatory gene, and most preferably the nucleotide sequence of interest comprises 16S ribosomal DNA (rDNA). In various embodiments, the delivery vehicle is a bacteriophage. Thus, various embodiments of the present invention include the use of CRISPR-Cas, with the recognition that this system can be employed to benefit human health by modifying the bacterial and other microbe communities that humans have long been exposed to in a fashion such that the beneficial aspects of such microbes can be preserved, while the disadvantageous aspects can be "cut out" of the microbe DNA—rather than attempting to change or modify the DNA of a human.

The present invention is one way in which human health concerns can be benefited directly by the use of a DNA deletion system without affecting the long term and permanent deletion of human genes. It is not believed to be obvious, let alone intuitive, that human health can be benefited by such a DNA deletion system used in a fashion that affects only gut microbes in a human's system.

Another aspect of the present invention includes the ability to load or impregnate mucosal strips with any number of active agents to achieve other desirable aspects, such as administration of particular vitamins, medicinal components, and certain CRISPR-Cas modified bacteria. In some embodiments the microbes are encapsulated within encapsulation structures selected to provide the desired degree of adhesion to the mucous membranes of the throat, gut, etc., and adapted to release the active ingredients slowly over time in situ. These encapsulation structures may be distributed within the base material in the strip composition. In one embodiment, the encapsulation structures comprise multilamellar microparticles. The multilamellar microparticles are selected to exhibit good adhesion to the mucous membranes of the throat, and are small enough to be effectively distributed in the strip. The strips of the present invention provide the requisite pliability and tensile strength necessary to securely adhere to a person's mucosal tissues for at least one hour, more preferably at least two hours, and preferably a bioadhesive polymer is selected from the group consisting of polycarbophil, carbomer, one or more acrylic polymers, one or more polyacrylic acids, copolymers of these polymers, a water soluble salt of a co-polymer of methyl vinyl ether and maleic acid or anhydride, a combination thereof and their salts. In certain embodiments, a mucosal adhesive strip has a coated surface for resisting bioadhesion that includes at least one patterned polymer including coating layer having a plurality of features attached to or projected into a base surface. The features each have at least one microscale (<1 mm) dimension and have at least one neighboring feature having a substantially different geometry. The patterned coating layer preferably provides an average roughness factor (R) of from 4 to 50. The coating layer resists or enhances bioadhesion as compared to the base surface. An article having a surface coating with topography for controlling bioadhesion comprises a base surface, at least one patterned polymer comprising coating layer including a plurality of spaced apart features attached to or projected into the base surface which provide at least a first feature spacing distance. The features each have at least one microscale dimension and at least one neighboring feature having a substantially different geometry. The coating layer provides an average roughness factor (R) of from 2 to 50, preferably being from 4 to 50. The coating layer resists or enhances bioadhesion as compared to the base surface.

Still other embodiments include the use of bacteria that have been modified to remove or disable one or more virulence factors of the particular bacteria. In this regard, one aspect of the present invention is directed to the modification of certain human-specific pathogens by targeting one or more virulence factors thereof, preferably by using CRISPR-Cas or CRISPR-Cpf1 systems, to excise virulence factors genes, or at least portions thereof or transcriptional or translational controls therefore, such that such pathogenic pathogens are deprived of their undesired pathogenic characteristics. One of skill in the art can readily assess the number and identity of human-specific pathogens, as well as the particular virulence factors associated therewith, and can then, employing the CRISPR systems as referenced herein, remove, render incapable or otherwise disable the virulence facts of such microorganisms such that they no long pose a pathogenic threat to humans. Certain embodiments provide for the delivery, via the strips as described herein, of one or more of the following microorganisms selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum,* and *Lactobacillus ingluviei*. The CRISPR-Cas system is preferreably employed to excise the virulence factors of one or more of the following bacteria: *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermen turn, Lactobacillus reuteri, Lactobacillus viridescens, Bifidobacterium bifidum, Lactobacillus ingluviei* and preferably selected from the group comprising the following microorganisms deposited with the German Collection for Microorganisms and Cell Cultures where they are numbered as DSM 25972, DSM 25987, DSM 25988, DSM 25989, DSM 25973 and have been in accordance with the Budapest Treaty regarding International Recognition of the Deposition of Microorganisms for the purpose of patent deposition. In a preferred embodiment of the invention, strips containing effective amounts of these bacteria are provided that are attached to the soft palate region of a person's mouth or on other mucosal surfaces. Other LAB that may be employed in various embodiments include the following: *lactobacillus slaivarius* CICC 23174; *lactobacillus plantarum* CGMCC 1.557, *lactobacillus rhamnosus* ATCC 53103, and *lactobacillus acidophilus* ATCC 4356.

Moreover, in preferred embodiments, the microbes modified are limited to those demonstrating human tropism such that undesired and unintended changes to other animals and organisms are not affected and that the only implications of such genomic alterations of human specific pathogens are restricted to such species in a manner that is not capable of affecting other than the particular human disease at issue. This can include, for example, modifications and/or employment of integrons, which are a two-component genetic recombination system present in the chromosome of many bacterial species. The integron incorporates mobile genes termed gene cassettes into a reserved genetic site via site-specific recombination, named the Integron/gene cassette system. The integron consists of three basic elements: an integrase gene, an attachment site and a promoter. These elements can be manipulated to, for example, decrease the ability of a particular bacteria in a person's gut from being able to effectively attach to epithelial tissue; or alternatively, to coaggregate with other bacteria.

To provide necessary and sufficient written disclosure and enablement of the various embodiments of the present invention, the following references are incorporated by reference in their entireties: U.S. Pat. No. 9,017,718 to Tan; 20140065218 to Lang et. al.; U.S. Pat. Nos. 6,599,883; 8,383,201; 5,158,789; 20070218114 to Sorousch; 20040136923 to Davidson; U.S. Pat. No. 8,999,372 to Davidson; 20090196907 to Bunick; 20090196908 to Lee; 20030124178 to Haley; 20070293587 to Haley; 20100285098 to Haley; 2006-0204591 to Burrell; U.S. Pat. No. 7,087,249 to Burrelll; U.S. Pat. No. 6,210,699 to Acharya; U.S. Pat. No. 8,865,211 to Tzannis; 20140199266 to Park; U.S. Pat. No. 6,599,883 to Romeo; PCT/US2008/080362 to Dussia; 2007-0218114 to Duggan; 20040136923 to Davidson; 20110142942 to Schobel; 20040120991 to Gardner et al.; Fuchs et al. U.S. Pat. No. 4,136,162; 20040136923 to Davidson; U.S. Pat. No. 4,163,777 to Mitra; U.S. Pat. No. 5,002,970 to Eby, III; 20040096569 to Barkalow et al.; 20060035008 to Virgallito et al.; 20030031737 to Rosenbloom; U.S. Pat. No. 6,919,373 to Lam et al.; 20050196358 to Georglades et al.; U.S. Pat. No. 3,832,460 to Kosti; 2002002057 to Battey et al.; 20040228804 to Jones, et al.; U.S. Pat. No. 6,054,143 to Jones; U.S. Pat. No. 5,719,196 to Uhari; 20150150792 to Klingman; 20140333003 to Allen; 20140271867 to Myers; 20140356460 to Lutin; 20150038594 to Borges; U.S. Pat. No. 6,139,861 to Friedman; 20150216917 to Jones; 20150361436 to Hitchcock; 20150353901 to Liu; U.S. Pat. No. 9,131,884 to Holmes; 20150064138 to Lu; 20150093473 to Barrangou; 20120027786 to Gupta; 20150166641 to Goodman; 20150352023 to Berg;

20150064138 to Lu; 20150329875 to Gregory; 20150329555 to Liras; 20140199281 to Henn; US20050100559 (proctor and Gamble); 20120142548 to Corsi et al.; U.S. Pat. No. 6,287,610, U.S. Pat. No. 6,569,474, US20020009520, US20030206995, US20070054008; and U.S. Pat. No. 8,349,313 to Smith; and U.S. Pat. No. 9,011,834 to McKenzie; 20080267933 to Ohlson et. al.; 20120058094 to Blasser et. al.; U.S. Pat. No. 8,716,327 to Zhao; 20110217368 to Prakash et. al.; 20140044734 to Sverdlov et al.; 20140349405 to Sontheimer; 20140377278 to Elinav; 20140045744 to Gordon; 20130259834 to Klaenhammer; 20130157876 to Lynch; 20120276143 to O'Mahony; 20150064138 to Lu; 20090205083 to Gupta et al.; 20150132263 to Liu; and 20140068797 to Doudna; 20140255351 to Berstad et al.; 20150086581 to Li; PCT/US2014/036849 and WO 2013026000 to Bryan.

Another aspect of certain embodiments of the present invention is directed to a thin film mucosal layered strip wherein modified bacteria (e.g via the CRISPR-Cas system) is encapsulated in a frangible enclosure and is present in an amount of at least about 0.5 ml. Other treatment agents may be encapsulated in such strips, such that antibiotics or co aggregation agents or LAB, etc. can be encapsulated in a manner that they can be released at a time when the person so desires and/or when the strip dissolves to a certain extent, e.g. when the walls of the encapsulating shell is worn thin enough to fracture to release the agent(s). The manner in which a capsule can be fractured in order to release its solvent contents is variable and will be understood by those of skill in the art. Preferably, the capsule is constructed in a manner that it is sufficiently robust such that mere transport and packaging of the strips containing such capsules does not cause any leakage or breakage of such capsules. Instead, the design of capsules is such that they are frangible with a considerable amount of force being directly applied thereto once the strips are placed on a particular mucosal surface, such as on the soft palette of a human, such that the person's tongue, when pressing against such capsule, can cause it to fracture to release the contents of the capsule. In other embodiments, two or more different materials may be released.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

What is claimed is:

1. A method for reducing the likelihood of developing non-alcoholic steatohepatitis (NASH) in an individual diagnosed with non-alcoholic fatty liver disease, comprising: providing in the gut of an individual a population of beneficial bacteria selected from the group consisting of *Lactobacillus* species; administering at least 6 grams per day of fiber to the individual to maintain a therapeutically effective amount of the beneficial bacteria in the gut of the individual; and inhibiting monoacylglycerolacyltransferase-3 (MGAT3) synthesis in the individual to lower triacylglycerol (TAG) production.

2. The method as set forth in claim 1, wherein the beneficial bacteria are present on a thin film mucosal layered strip, said beneficial bacteria being encapsulated in a frangible enclosure.

3. The method as set forth in claim 1, further comprising inhibiting expression of diacylglycerolacyltransferase-2 (DGAT-2) in said individual.

4. The method as set forth in claim 1, further comprising increasing the levels of *Roseburia*, while reducing the levels of *Akkermansia* spp. in the individual's gut microbiome.

5. The method as set forth in claim 4, wherein the population of beneficial bacteria include bacteria that have been modified to increase the level of butyrate.

6. A method for reducing the likelihood of developing non-alcoholic steatohepatitis (NASH) in an individual diagnosed with non-alcoholic fatty liver disease, comprising: providing in the gut of an individual a population of beneficial bacteria selected from the group consisting of *Lactobacillus* species; administering at least 6 grams per day of fiber to the individual to maintain a therapeutically effective amount of the beneficial bacteria in the gut of the individual; and inhibiting expression of diacylglycerolacyltransferase-2 (DGAT-2) in said individual.

7. The method as set forth in claim 6, further comprising increasing the levels of *Roseburia*, while reducing the levels of *Akkermansia* spp. in the individual's gut microbiome.

8. The method as set forth in claim 6, wherein the beneficial bacteria are present on a thin film mucosal layered strip, said beneficial bacteria being encapsulated in a frangible enclosure.

9. The method as set forth in claim 6, wherein the population of beneficial bacteria include bacteria that have been modified to increase the level of butyrate.

10. A method for reducing the likelihood of developing non-alcoholic steatohepatitis (NASH) in an individual diagnosed with non-alcoholic fatty liver disease, comprising: providing in the gut of an individual a population of beneficial bacteria selected from the group consisting of *Lactobacillus* species; administering at least 6 grams per day of fiber to the individual to maintain a therapeutically effective amount of the beneficial bacteria in the gut of the individual; and increasing the levels of *Roseburia*, while reducing the levels of *Akkermansia* spp. in the individual's gut microbiome.

11. The method as set forth in claim 10, further comprising inhibiting expression of diacylglycerolacyltransferase-2 (DGAT-2) in said individual.

12. The method as set forth in claim 10, wherein the beneficial bacteria are present on a thin film mucosal layered strip, said beneficial bacteria being encapsulated in a frangible enclosure.

13. The method as set forth in claim 10, wherein the population of beneficial bacteria include bacteria that have been modified to increase the level of butyrate.

* * * * *